United States Patent
Wakai et al.

(10) Patent No.: US 11,295,447 B2
(45) Date of Patent: Apr. 5, 2022

(54) SYSTEM, PROGRAM, AND METHOD FOR DETERMINING HYPERMUTATED TUMOR

(71) Applicants: Niigata University, Niigata (JP); Denka Company Limited, Tokyo (JP)

(72) Inventors: Toshifumi Wakai, Niigata (JP); Shujiro Okuda, Niigata (JP); Yoshifumi Shimada, Niigata (JP); Hiroshi Izutsu, Machida (JP); Keisuke Kodama, Machida (JP)

(73) Assignees: Niigata University, Niigata (JP); Denka Company Limited, Tokyo (JP)

( * ) Notice: Subject to any disclaimer, the term of this patent is extended or adjusted under 35 U.S.C. 154(b) by 51 days.

(21) Appl. No.: 16/964,550

(22) PCT Filed: Feb. 7, 2019

(86) PCT No.: PCT/JP2019/004499
§ 371 (c)(1),
(2) Date: Jul. 23, 2020

(87) PCT Pub. No.: WO2019/159821
PCT Pub. Date: Aug. 22, 2019

(65) Prior Publication Data
US 2021/0035300 A1 Feb. 4, 2021

(30) Foreign Application Priority Data
Feb. 15, 2018 (JP) ............... JP2018-024784

(51) Int. Cl.
*G06K 9/00* (2006.01)
*G06T 7/00* (2017.01)
(Continued)

(52) U.S. Cl.
CPC ............. *G06T 7/0014* (2013.01); *G01N 1/30* (2013.01); *G01N 33/4833* (2013.01);
(Continued)

(58) Field of Classification Search
CPC ......... G06T 7/0014; G06T 2207/10024; G06T 2207/20021; G06T 2207/20081;
(Continued)

(56) References Cited

U.S. PATENT DOCUMENTS

2014/0193060 A1 7/2014 Tanji
2017/0039712 A1 2/2017 Tanji
(Continued)

FOREIGN PATENT DOCUMENTS

CN 107064019 A 8/2017
JP 2004-346911 A 12/2004
(Continued)

OTHER PUBLICATIONS

Islam Hassan1, Aikaterini Kotrotsou2, Carlos Kamiya Matsuoka1; "NIMG-28. Increased Mutation Burden (Hypermutation) in Gliomas is Associated With a Unique Radiomic Texture Signature in Magnetic Resonance Imaging", Neuro Oncol. Nov. 2017; 19 (Suppl 6): vi147-vi148. Published online Nov. 6, 2017 (Year: 2017).*
(Continued)

*Primary Examiner* — Atiba O Fitzpatrick
(74) *Attorney, Agent, or Firm* — Christensen O'Connor Johnson Kindness PLLC

(57) ABSTRACT

A method, a program, and a method determining hypermutated type cancer with higher accuracy than before is provided.
Provided is a system for determining hypermutated cancer comprising, an input unit configured to be capable of inputting a plurality of first image data, a plurality of second image data and a plurality of third image data, wherein the first image data represents an image of a pathological section of stained hypermutated cancer, the second image data represents an image of a pathological section of cancer which is not hypermutated, and is stained same as the
(Continued)

pathological section of the first image data, and the third image data represents an image of a pathological section of cancer which is newly determined whether hypermutated or not, and is stained same as the pathological section of the first image data, a holding unit configured to be capable of holding a first image data and a second image data, a machine learning execution unit configured to be capable of generating a determination model determining whether a cancer is hypermutated or not, using the first image data and the second image data held by the holding unit as training data, and a determining unit configured to be capable of determining whether the third image data represents an image of hypermutated cancer or not, by inputting the third image data into the determination model.

13 Claims, 12 Drawing Sheets

(51) Int. Cl.
 *G01N 1/30* (2006.01)
 *G01N 33/483* (2006.01)
(52) U.S. Cl.
 CPC .................. *G01N 2001/302* (2013.01); *G06T 2207/10024* (2013.01); *G06T 2207/20021* (2013.01); *G06T 2207/20081* (2013.01); *G06T 2207/30028* (2013.01); *G06T 2207/30096* (2013.01)
(58) Field of Classification Search
 CPC ........... G06T 2207/30028; G06T 2207/30096; G01N 1/30; G01N 33/4833; G01N 2001/302
 See application file for complete search history.

(56) References Cited

U.S. PATENT DOCUMENTS

| | | |
|---|---|---|
| 2017/0370901 A1 | 12/2017 | Ichitani |
| 2018/0204048 A1 | 7/2018 | Chefd'hotel et al. |
| 2018/0204324 A1 | 7/2018 | Kawaguchi et al. |
| 2018/0225424 A1* | 8/2018 | Kaditz .................. G16H 50/20 |
| 2019/0332963 A1* | 10/2019 | Wong .................... G06N 20/00 |

FOREIGN PATENT DOCUMENTS

| | | |
|---|---|---|
| JP | 2015-052581 A | 3/2015 |
| WO | 2016/093090 A1 | 6/2016 |
| WO | 2017/010397 A1 | 1/2017 |
| WO | 2017/037180 A1 | 3/2017 |

OTHER PUBLICATIONS

Briggs, S., and I. Tomlinson, "Germline and Somatic Polymerase ∈ and σ Mutations Define a New Class of Hypermutated Colorectal and Endometrial Cancers," Journal of Pathology 230-148-153, 2013.
Guedes, L.B., et al., "MSH2 Loss in Primary Prostate Cancer, Clinical Cancer Research," 23(22):6863-6874, Nov. 2017.
International Search Report dated May 7, 2019, issued in corresponding International Application No. PCT/JP2019/004499, filed Feb. 7, 2019, 2 pages.
Rizvi, N.A., et al., "Mutational Landscape Determines Sensitivity to PD-1 Blockade in Non-Small Cell Lung Cancer," Science 348(6230):124-128, Apr. 2015. (Author Manuscript provided, PMCID: PMC4993154, available in PMC Aug. 22, 2016, 12 pages.).
Roberts, S.A., and D.A. Gordenin, "Hypermutation in Human Cancer Genomes: Footprints and Mechanisms," Nature Reviews Cancer 14(12):786-800, Dec. 2014.
Tracey, L., et al., "Somatic Hypermutation Signature in B-Cell Low-Grade Lymphomas," Haematologica 93(8):1186-1194, 2008.
Yuza, K., et al., "Hypermutation and Microsatellite Instability in Gastrointestinal Cancers," Oncotarget 8(67):112103-112115, Dec. 2017.
Extended European Search Report dated Mar. 16, 2021, issued in corresponding Application No. 19753904.2, filed Feb. 7, 2019, 9 pages.
Schaumberg, A.J., et al., "H&E-stained Whole Slide Image Deep Learning Predicts SPOP Mutation State in Prostate Cancer," bioRxiv, Mar. 3, 2017, pp. 1-11.
Yoon, W.B., et al., "Methods of Hematoxylin and Erosin Image Information Acquisition and Optimization in Confocal Microscopy," Healthcare Informatics Research (HIR): Image Conversion in Confocal Microscopy 22(3): 238-242, Jul. 1, 2016.
Office Action dated Dec. 16, 2021, issued in corresponding CN Application No. 201980013657.2, filed Feb. 7, 2019, 14 pages.
Communication pursuant to Article 94(3) EPC, dated Dec. 17, 2021, issued in corresponding EP Application No. 19 753 904.2, 9 pages.
Kuru, K., "Optimization and enhancement of H&E stained microscopical images by applying bilinear interpolation method on lab color mode", Theoretical Biology and Medical Modelling, BIOMED Central LTD., London, GB, vol. 11, No. 1, Feb. 6, 2014, p. 9, XP021176077, ISSN: 1742-4682, DOI: 10.1186/1742-4682-11-9.

* cited by examiner $w_{j,i}^{n,n-1}$ : Weight between the calculation nodes j-th in n-th layer and i-th in (n-1) th (-1 to 1)

$f()$ : Activation function $b_j^n$ : Bias of the j-th in n-th layer

SYSTEM, PROGRAM, AND METHOD FOR DETERMINING HYPERMUTATED TUMOR

TECHNICAL FIELD

The present invention relates to hypermutated type cancer determining system, program, and method.

BACKGROUND ART

By extensively examining cancer gene mutations, it has become clear that cancers can be classified according to the pattern of gene mutations. One of the characteristic mutation patterns of cancer is hypermutated type. Hypermutated cancers are distinguished by a higher somatic mutation rate than other types. Some cancer such as gastric cancer, breast cancer, colon cancer, glioblastoma, and uterine cancer are known to occasionally show hypermutated feature. Hypermutated cancer often also have the property of microsatellite instability, which shows defects or imperfections in the mismatch repair mechanism during DNA replication. It is considered that this is because the genes of MLH1, MLH3, MSH2, MSH3, MSH6 and PMS2 which are mismatch repair enzymes are mutated and the expression of MLH1 gene is suppressed by methylation. It is also known that mutation of polymerase ε (POLE), which is a DNA replication enzyme, causes somatic mutation at a particularly high frequency, resulting in hypermutated type (Non-Patent Documents 1 and 2).

Meanwhile, the mechanism of cancer immune escape has been elucidated, and new cancer immunotherapy methods targeting this mechanism have been clinically applied. Among them, the characteristic method is used PD-1 (Programmed cell Death-1)/PD-L1 (PD-1 Ligand1) route, which is also called the immuno-checkpoint route. By blocking the immunosuppressive auxiliary signal PD-1/PD-L1 route, immunosuppression of T cells is released, and T cells are activated to suppress tumors expressing cancer-specific antigens. In addition, CTLA-4 is also expressed on activated T cells, and when the CD28 ligand of antigen presenting cells binds, T cell activation is suppressed. Therefore, blocking this route also releases T cell immunosuppression, it is possible to cause tumor suppression. Anticancer agents applying such principles have been put into practical use (for example, nivolumab, ipilibumab et al.).

Furthermore, there are other such immunosuppressive mechanisms, and it is expected that antitumor agents that block these immunosuppressive mechanisms will be developed and put into practical use in the future. Since hypermutated cancer have many cancer-specific antigens that are the targets of the immune system, it has been shown that therapies that block the immunosuppressive signaling route are highly effective. Thus, a method capable of easily determining whether the cancer is hypermutated or not is demanded (Non-Patent Document 3).

Conventionally, in order to test hypermutated type cancer, a method of performing comprehensive gene analysis and counting the number of mutations is known, but there is a problem that the test requires a lot of labor and time. Further, there is also known a method of examining a defect or imperfections of the mismatch repair mechanism, which is one of the causes of hypermutation in cancer, by immunostaining of a related gene or a microsatellite instability test. But all hypermutated cancer cannot be detected by the method.

On the other hand, a pathological diagnosis support program as disclosed in Patent Document 1 is known.

CITATION LIST

非特許文献

Non-Patent Literature 1: Nat Rev Cancer. 2014 December; 14(12):786-800
Non-Patent Literature 2: J Pathol 2013; 230:148-153
Non-Patent Literature 3: Science 3 Apr. 2015 Vol. 348, Issue 6230, pp. 124-128

Patent Literature

Patent Literature 1: Japanese Patent Application No. 2004-346911

SUMMARY OF INVENTION

Technical Problem

In Patent Document 1, it is possible to determine the presence or absence of a tumor and whether it is benign or malignant, but no reference is made to a method for determining hypermutated cancer.

The present invention has been made in view of such circumstances, and provides a method, a program and a method determining hypermutated cancer with higher accuracy than ever before.

Solution to Problem

Provided is a system for determining hypermutated cancer comprising, an input unit configured to be capable of inputting a plurality of first image data, a plurality of second image data and a plurality of third image data, wherein the first image data represents an image of a pathological section of stained hypermutated cancer, the second image data represents an image of a pathological section of cancer which is not hypermutated, and is stained same as the pathological section of the first image data, and the third image data represents an image of a pathological section of cancer which is newly determined whether hypermutated or not, and is stained same as the pathological section of the first image data, a holding unit configured to be capable of holding a first image data and a second image data, a machine learning execution unit configured to be capable of generating a determination model determining whether a cancer is hypermutated or not, using the first image data and the second image data held by the holding unit as training data, and a determining unit configured to be capable of determining whether the third image data represents an image of hypermutated cancer or not, by inputting the third image data into the determination model.

According to the present invention, determination model determining whether a cancer is hypermutated or not using the first image data and the second image data is generated. Here, the first image data represents an image of a pathological section of stained hypermutated cancer. And the second image data represents an image of a pathological section of cancer which is not hypermutated, and is stained same as the pathological section of the first image data. The determining unit configured to be capable of determining whether the third image data represents an image of hypermutated cancer or not, by inputting the third image data into the determination model. The third image data represents an image of a pathological section of cancer which is newly determined whether hypermutated or not, and is stained same as the pathological section of the first image data. As a result, it is possible to quickly and accurately determine whether the cancer is hypermutated or not, which has been difficult in the past without genetic analysis using a next-generation sequencer, etc., and to select an effective drug for treatment.

Hereinafter, various embodiments of the present invention will be exemplified. The embodiments described below can be combined with each other.

Preferably, a method of staining the pathological section is hematoxylin eosin staining.

Preferably, the input unit is configured to be capable of further inputting non-cancer image data, the non-cancer image data represents an image which is not a pathological section of cancer, the holding unit is configured to be capable of further holding the non-cancer image data, the machine learning execution unit is configured to be capable of further generating a determination model determining whether an image represents a pathological section of cancer or not, using the non-cancer image data held by the holding unit as training data, the determining unit is configured to be capable of further determining whether the third image data represents an image of cancer or not.

Preferably, an image processing unit configured to be capable of performing a Z value conversion process for at least one of the first image data, the second image data and the non-cancer image data, converting each RGB color in each pixel into Z value in the CIE color system based on the entire color distribution of the first image data, the second image data or the non-cancer image data.

Preferably, the image processing unit is configured to be capable of performing a division process dividing at least one of the first image data, the second image data, and the non-cancer image data input into the input unit.

Preferably, the division process is configured to be capable of performing division process dividing image data of the same pathological section on at least one of the first image data and the second image data.

Preferably, the image processing unit performs the division process such that a part of the regions in a divided image overlaps each other.

Preferably, the image processing unit is configured to be further capable of performing a division process dividing the third image data input into the input unit.

Preferably, the determining unit determines whether the third image data represents an image of a pathological section of cancer or not, and further determines whether the image data determined as a cancer image data represents an image of hypermutated cancer or not.

Preferably, the determining unit determines whether a cancer image data represents an image of hypermutated cancer or not, based on the ratio of the image data determined as an image of hypermutated cancer in the cancer image data.

Further provided is a non-transitory computer-readable storage medium storing a program for causing a computer to perform a process comprising, inputting a plurality of first image data and a plurality of second image data, wherein the first image data represents an image of a pathological section of stained hypermutated cancer and the second image data represents an image of a pathological section of cancer which is not hypermutated, and is stained same as the pathological section of the first image data, holding a first image data and a second image data, and generating a determination model determining whether a cancer is hypermutated or not, using the first image data and the second image data held by the holding unit as training data.

Further provided is a method of determining hypermutated cancer performed by the system described above.

Further provided is a method of determining hypermutated cancer performed by the program stored in the storage medium described above.

Preferably, the method described above includes the process of determining the effectiveness of immune checkpoint inhibitors.

DESCRIPTION OF EMBODIMENTS

An embodiment of the present invention will be described below with reference to the drawings. The various features shown in the embodiments described below can be combined with each other.

1. FIRST EMBODIMENT 1.1. Determining Whether a Cancer is Hypermutated or Not

A system 10 according to an embodiment of the present invention will be described below with reference to FIG. 1 to FIG. 4.

1.1.1. System 10

Figure 1:
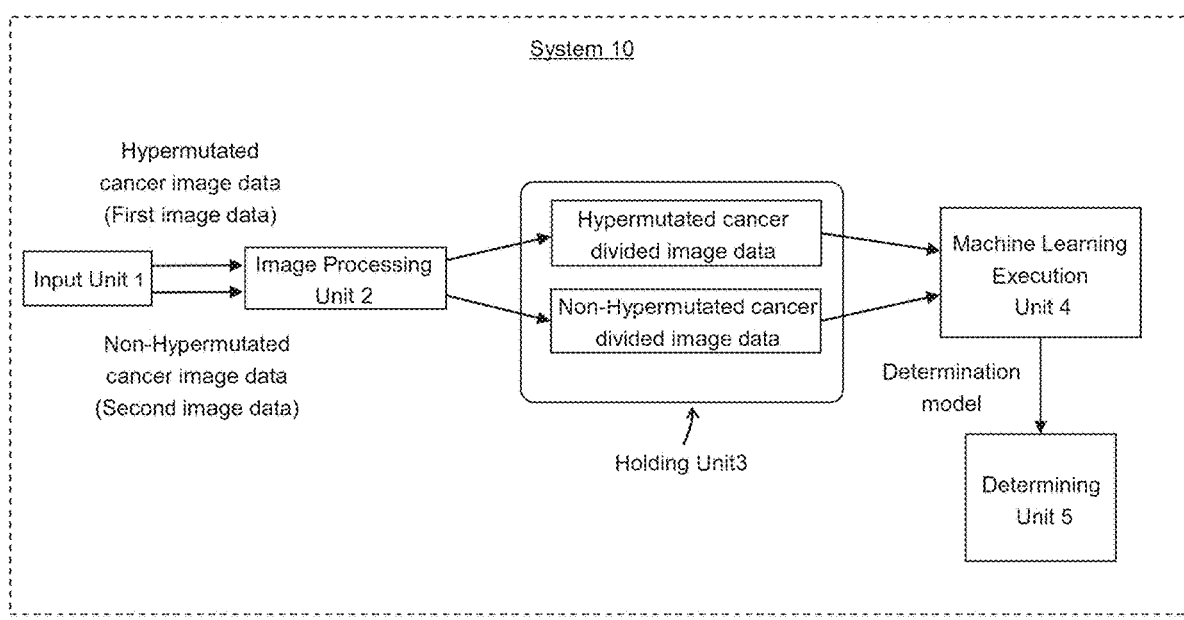
FIG. 1 is a functional block diagram of a system 10 according to a first embodiment of the present invention.

As shown in FIG. 1, the system 10 includes an input unit 1, an image processing unit 2, a holding unit 3, a machine learning execution unit 4, and a determining unit 5.

The input unit 1 is configured to be capable of inputting a plurality of first image data, a plurality of second image data, and a plurality of third image data. Here, the first image data represents an image of a pathological section of stained hypermutated cancer. The second image data represents an image of a pathological section of cancer which is not hypermutated, and is stained same as the pathological section of the first image data. The third image data represents an image of a pathological section of cancer which is newly determined whether hypermutated or not, and is stained same as the pathological section of the first image data. Here, in the present embodiment, the RGB values of these image data can take value from 0 to 255.

In the present embodiment, pathological tissue stained specimens of each 17 cases which are colorectal cancer samples determined to be Hypermutation type or Non-Hypermutation type by analysis of cancer genomic DNA sequence, were obtained. Here, 17 cases had been determined to be Hypermutated as a result of cancer genome sequencing in 201 Japanese colon cancer patients (reference: Nagahashi et al GenomeMed 2017). Then, a pathological tissue stained specimen of colorectal cancer obtained by hematoxylin eosin staining was used as the first image data and the second image data by a digital pathology technique. Here, in this embodiment, the first image data and the second image data are stored as digital pathology image data conforming to the MIRAX format. Note that the above condition is not limited to this, and a predetermined number of cases of cancer samples other than colorectal cancer may be acquired.

As described above, in this embodiment, since the image data stained with hematoxylin/eosin, which is used in many clinical cases, is adopted as the first image data and the second image data, it is possible to realize a highly versatile determining system.

However, other staining methods can be used depending on the conditions. Furthermore, the storage format of the image data is not limited to this.

The image processing unit 2 is configured to be capable of performing a division process dividing a plurality of the first image data, the second image data, and the third image data input to the input unit 1. In this embodiment, the image processing unit 2 has a function of dividing the first image data, the second image data, and the third image data into predetermined tiles. As an example, the image processing unit 2 divides the first image data, the second image data, and the third image data into 300-pixel×300-pixel size images (as tiles). The division size is not particularly limited, but it is preferable that the size is such that whether or not the image data represents a cancer tissue site can be identified. In this embodiment, each of the first image data and the second image data is divided into 1000 or more tiles by the division processing. Further, in the present embodiment, the image processing unit 2 is configured to be capable of performing a division process dividing image data of the same pathological section as at least one of the first image data and the second image data. Note that the division size and the number are not limited to this, and any conditions can be adopted.

In this way, by dividing the image data input to the input unit 1, it is possible to increase the number of pieces of training data used for subsequent machine learning and to improve the accuracy of the machine learning.

In addition, in the present embodiment, image processing unit 2 configured to be capable of performing a Z value conversion process for divided first image data and divided second image data, converting each RGB color in each pixel into Z value in the CIE color system based on the entire color distribution of the first image data and the second image data. Specifically, the Z value has a normal distribution centered on 0, and the RGB value of the image data takes value from 0 to 255. Thus, it is desirable that the Z value of each RGB color is kept in the double range of the standard deviation ($\sigma$). Therefore, the image processing unit 2 has a function of correcting a value more than $2\sigma$ to $2\sigma$ and a value less than $-2\sigma$ to $-2\sigma$. Further, the image processing unit 2 has a function of adding 2 to these values to convert all the values into values of 0 or more, and then dividing by 4 to standardize the values from 0 to 1. Further, the image processing unit 2 has a function of multiplying such a value by 255 to convert it into a normal color expression value. In addition, the image processing unit 2 also performs a process of truncating the decimal places so that the value becomes integer. Note that the standardization method is not limited to this.

Here, if "x=int(((min(max(xz,−2),2)+2)/4)×255)" is defined, "xz=z-valued RGB value" is established.

In this way, by converting the RGB colors of the first image data and the second image data into Z values, it is possible to reduce the variation of color (that is shade or color) in the staining process, and to suppress the influence on the subsequent machine learning. As a result, it is possible to improve the accuracy of the machine learning.

The holding unit 3 is configured to be capable of holding the first image data and the second image data. Here, the holding unit 3 is configured by an arbitrary memory, latch, HDD, SSD, or the like.

The machine learning execution unit 4 is configured to be capable of generating a determination model determining whether cancer is a hypermutated or not, using the first image data and the second image data held by the holding unit 3 as training data. Details of the determination model will be described later with reference to FIG. 3.

The machine learning algorithm of the machine learning execution unit 4 is not particularly limited, but, for example, a neural network or deep learning can be used. In addition, for example, a CNN (Convolutional Neural Network) for image identification called "Inception-v3" developed by Google Inc. Such a CNN can be implemented using the "Keras" framework. For machine learning itself, in order to prevent over-learning, the "Early Stopping" method is used, in which the accuracy of the model under learning is calculated using the image of the validation set for each 1 epoch, and the learning is stopped at the epoch in which the fluctuation of the accuracy index has subsided. In the present embodiment, machine learning is repeatedly for 14 epoch executed in Z-value learning.

The determining unit 5 is configured to be capable of determining whether the third image data represents an image of hypermutated cancer or not, by inputting the third image data into the determination model.

1.1.2. Flow Chart

Figure 2:
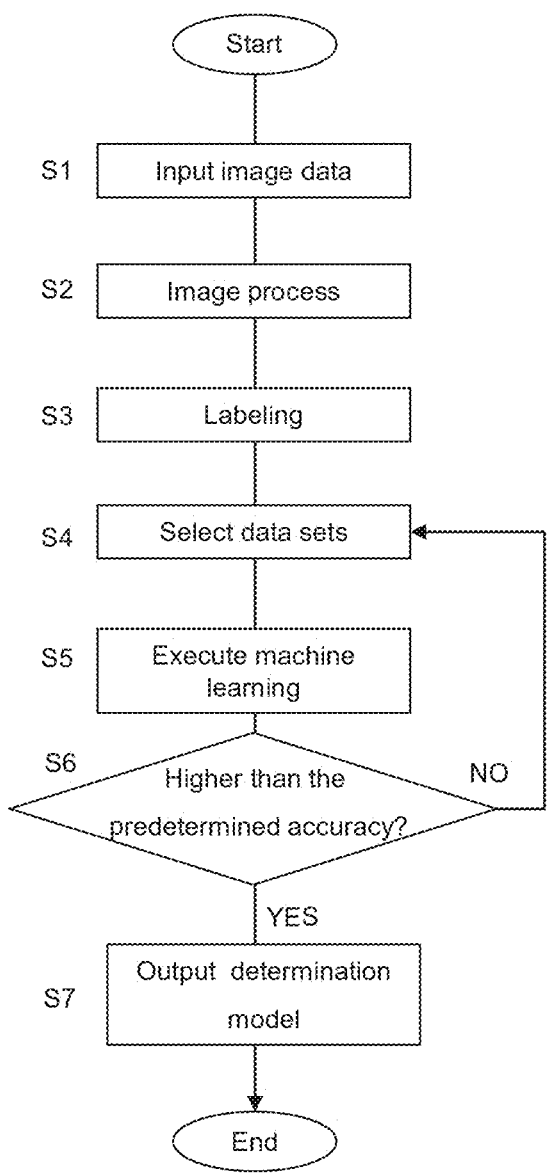
FIG. 2 is a flowchart showing a flow of generating a determination model determining whether or not the cancer is hypermutated according to the first embodiment of the present invention.

Next, with reference to FIG. 2, a flow of generating a determination model determining whether the cancer is a hypermutated or not according to an embodiment of the present invention will be described.

First, in S1, the first image data and the second image data are input into the input unit 1.

Next, in S2, the image processing unit 2 performs a division process dividing the first image data and the second image data. In this embodiment, each of the first image data and the second image data is divided into 1000 or more tiles. The number of divisions can be set as appropriate, and may be, for example, 1000 to 3000, preferably 1000 to 2000, and more preferably 1000 to 1500. Specifically, the number may be, for example, 1000, 1100, 1200, 1300, 1400, 1500, 1600, 1700, 1800, 1900, 2000, 2100, 2200, 2300, 2400, 2500, 2600, 2700, 2800, 2900, 3000. And the number also may be within a range between any two of the values exemplified here.

At the same time, the image processing unit 2 performs a Z-value conversion process converting the divided first image data and second image data into Z value in the CIE color system.

Next, in S3, with respect to the Z-valued first image data and second image data, each image data is determined as image data representing hypermutated cancer or non-hypermutated cancer, and each image data is labeled.

Next, in S4, image data of 13 cases used for machine learning by the machine learning execution unit 4 is selected from the first image data and the second image data of 17 cases input to the input unit 1. Such selection may be done randomly or by a cancer pathologist. Then, the labeled first image data and second image data are held in the holding unit 3. The first image data and the second image data correspond to "correct answer set" in machine learning.

Next, in S5, the machine learning execution unit 4 executes machine learning to generate a determination model determining whether the cancer is hypermutated or not, using the first image data and the second image data held by the holding unit 3 as training data. Specifically, using the first image data and the second image data of 13 cases labeled in S4, machine learning for determining whether or not an image data represents hypermutated cancer or not is performed.

Next, in S6, whether or not the accuracy of the determination model is equal to or higher than a predetermined accuracy is judged. When the accuracy of the determination model is not equal to or higher than the predetermined accuracy (the judgement is NO), the S4 is performed again, and the image data of 13 cases of different combinations is selected from the first image data and the second image data of 17 cases, and the process in S5 is executed. On the other hand, when the accuracy of the determination model is equal to or higher than the predetermined accuracy (the judgement is YES), the determination model is adopted, and the process proceeds to S7.

Finally, in S7, the determining unit 5 outputs the determination model determined in S6 and stores the model in the holding unit 3 or a storage unit (not shown).

1.1.3. Determination of Whether the Cancer is Hypermutated or Not

Next, the flow of the third image data determining whether the third image data is hypermutated or not using a determination model will be described with reference to FIG. 3 and FIG. 4.

Figure 3:
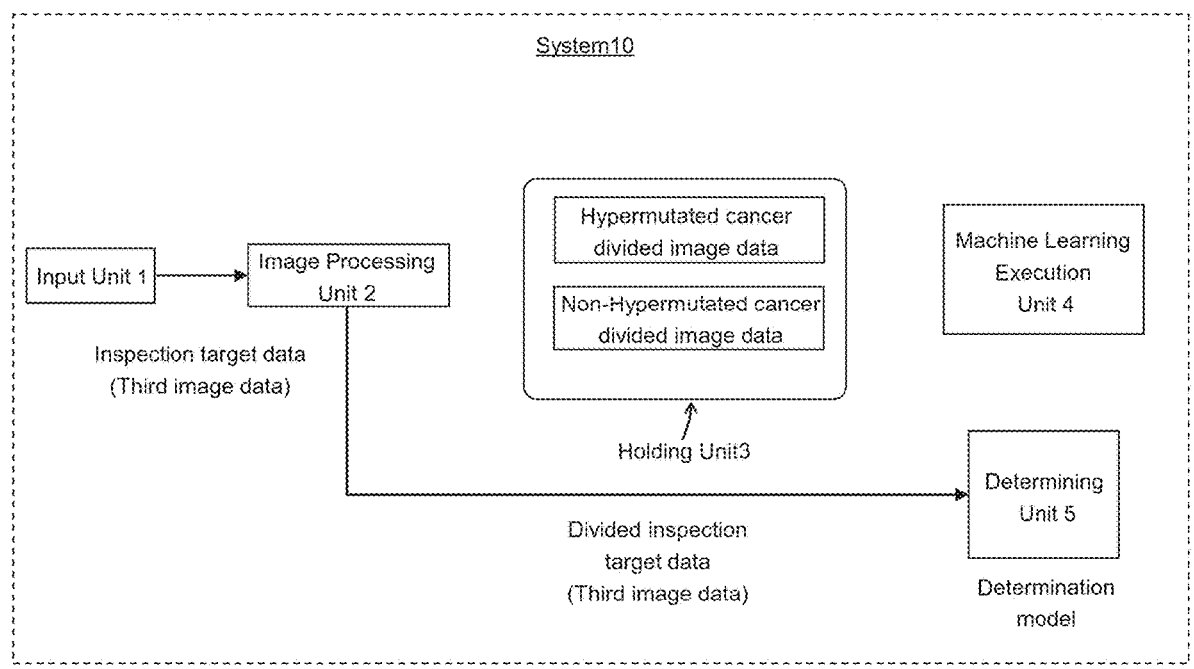
FIG. 3 is a conceptual diagram showing a flow of third image data when it is determined whether or not the third image data represents a hypermutated type cancer using a determination model.

As shown in FIG. 3, in the present embodiment, the third image data input into the input unit 1 is output to the image processing unit 2 and the third image data on which the above-described image processing (division process and Z-value conversion process) performed is output to the determining unit 5. Then, the determining unit 5 determines whether the third image data is hypermutated or not by using the determination model output in S7 of FIG. 2.

In this way, by performing the division process also on the third image data, the size of the image data to be determined and the sizes of the first and second image data are matched, and the determination accuracy in the determining unit 5 can be improved.

The flow chart at this time is as follows.

Figure 4:
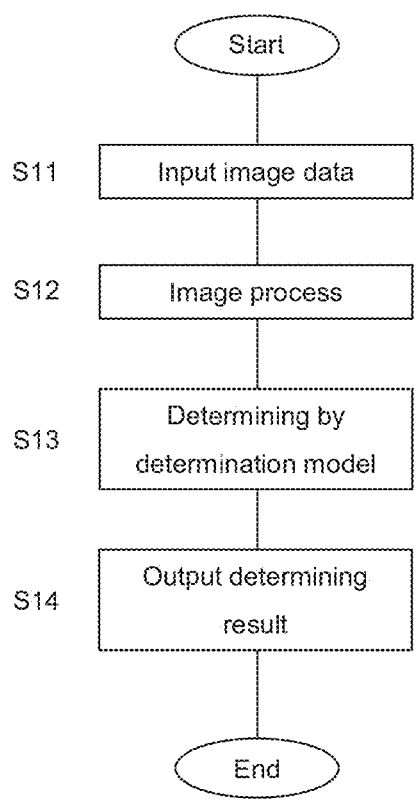
FIG. 4 is a flowchart showing a flow of determining whether or not the cancer is hypermutated according to the first embodiment of the present invention.

As shown in FIG. 4, first, in S11, the third image data is input into the input unit 1.

Next, in S12, the image processing unit 2 performs image process (division process and Z-value conversion process).

Next, in S13, the determining unit 5 determinates whether the third image data represents hypermutated cancer or not by using the determination model described above.

Finally, in S14, the determination result by the determining unit 5 is output. The output mode of the determination result is not particularly limited. For example, the result may be expressed by the comments as "Hypermutated Cancer", "Not Hypermutated Cancer", "The probability of hypermutated cancer is X %", etc.

1.1.4. Determination by Determination Model

Next, the determination using the determination model in S13 of FIG. 4 will be described with reference to FIG. 5 and FIG. 6. In this embodiment, the machine learning algorithm is not particularly limited, and a neural network or deep learning can be used. Hereinafter, for simplification of description, an example using a neural network will be described.

Figure 5:
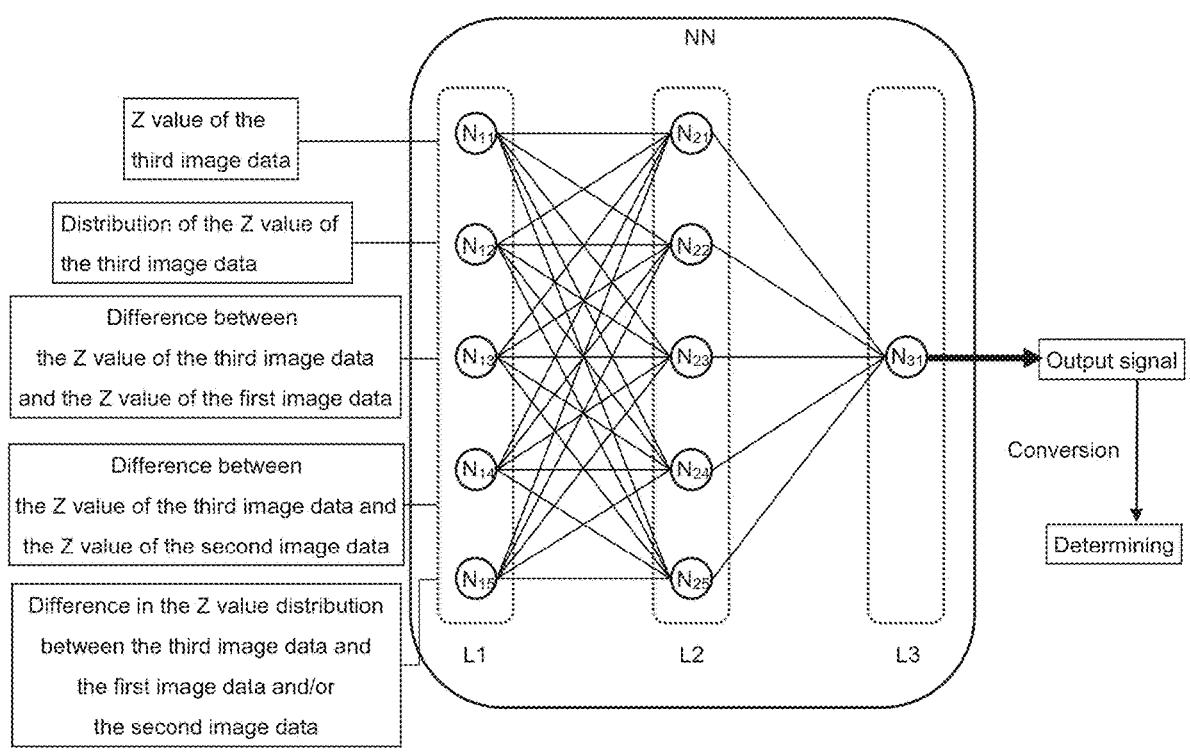
FIG. 5 is a conceptual diagram explaining the analysis in S13 of FIG. 4.
Figure 6:
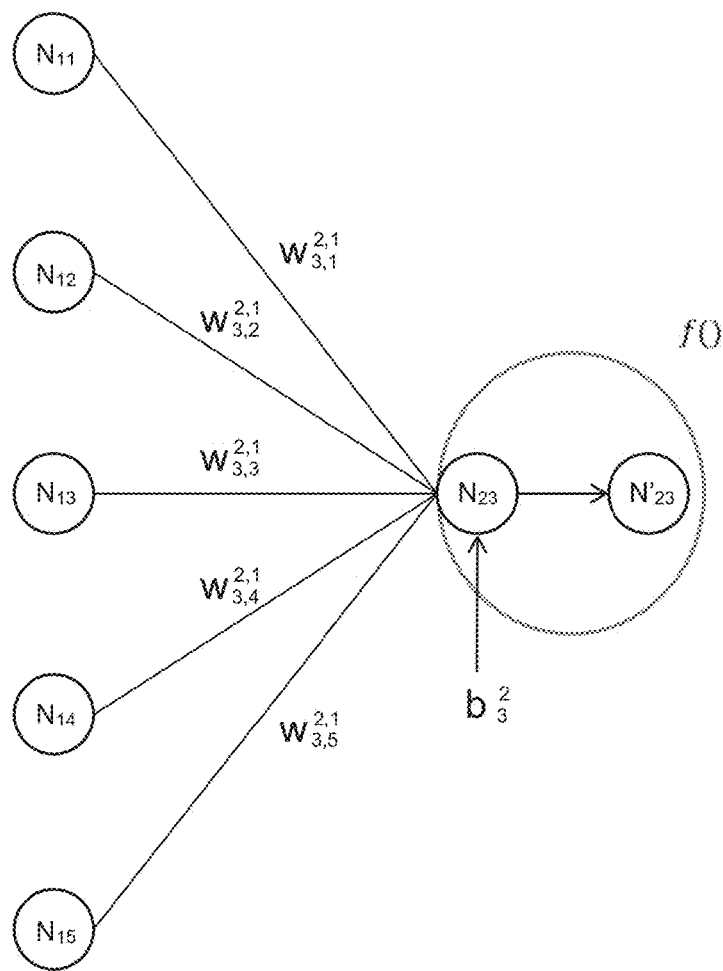
FIG. 6 is a conceptual diagram explaining a weight w in a determination model.

As shown in FIG. 5, a neural network (hereinafter referred to as NN in the drawing) is composed of a plurality of layers (first layer L1 to third layer L3) and a plurality of calculation nodes N (N11 to N31). Here, Nij represents the j-th calculation node N in the i-th layer. In this embodiment, the neural network is constructed with $i=3$ and $j=5$. The values of i and j are not limited to these values, and may be integers between $i=1$ to 100 and $j=1$ to 100 or integers of 100 or more, for example.

Also, a predetermined weight w is set to each calculation node N. As shown in FIG. 4, for example, when focusing on the calculation node N23 of the second layer, the weight w is set between the calculation node N23 and all the calculation nodes N11 to N15 in the previous first layer. The weight w is set to a value of −1 to 1, for example.

The machine learning execution unit 4 inputs various parameters to the neural network. In the present embodiment, the parameters input to the neural network is the Z value of the third image data, the distribution of the Z value of the third image data, the difference between the Z value of the third image data and the Z value of the first image data, the difference between the Z value of the third image data and the Z value of the second image data, and the difference in the Z value distribution between the third image data and the first image data and/or the second image data. Here, the Z value of the first to third image data is Z value in each pixel. The distribution of Z values of the first to third image data is the distribution of Z values in each image data (300 pixels×300 pixels). Further, the difference in the Z value distribution between the third image data and the first image data and/or the second image data is the difference in the Z value distribution of the third image data and of the corresponding pixel of the first image data and/or the second image data. Also, the difference in the Z value distribution may be the sum of the differences in the Z values of corresponding pixel in each image data.

Here, as described above, each parameter is normalized to a value of 0 to 1 to be input into the neural network. For example, when the input parameter is 0, 0 is input as the input signal. When the input parameter is 1, 1 is input as the input signal.

Then, the determining unit 5 inputs the input signal specified by various parameters into the first layer L1. Such input signals are output from the calculation nodes N11 to N15 of the first layer to the calculation nodes N21 to N25 of the second layer L2, respectively. At this time, the values output from the calculation nodes N11 to N15 are multiplied by the weight w set for each calculation node N, and the obtained values are input into the calculation nodes N21 to N25. The calculation nodes N21 to N25 sum the input values, add the bias b shown in FIG. 6, and input the obtained value into the activation function f( ). Then, the output value from the activation function f( ) (in the example of FIG. 6, the output value from the virtual calculation node N'23) is transmitted to the next calculation node N31. At this time, the weight w set between the calculation nodes N21 to N25 and the calculation node N31 is multiplied by the output values from the calculation nodes N21 to N25, and the obtained value is input into the calculation node N31. The calculation node N31 sums the input values and outputs the obtained value as an output signal. At this time, the calculation node N31 may sum input values, input a value obtained by adding a bias value to the total value to the activation function f( ), and may output the value as an output signal. Here, in the present embodiment, the value of the output signal is adjusted to be a value of 0 to 1. Then, the machine learning execution unit 4 outputs the value corresponding to the value of the output signal as the probability of determining whether the cancer is hypermutated or not.

As described above, the system 10 according to the present embodiment uses the first image data and the second image data as the training data and performs the machine learning by the machine learning execution unit 4 to generate a determination model (neural network and weight w) determining whether the cancer is hypermutated or not. Then, the determination unit 5 determinates whether the third image data represents hypermutated cancer or not by using the determination model.

1.2. Generation of Determination Model

Next, the generation of the determination model in S5 to S6 of FIG. 2 will be described with reference to FIG. 7.

Figure 7:
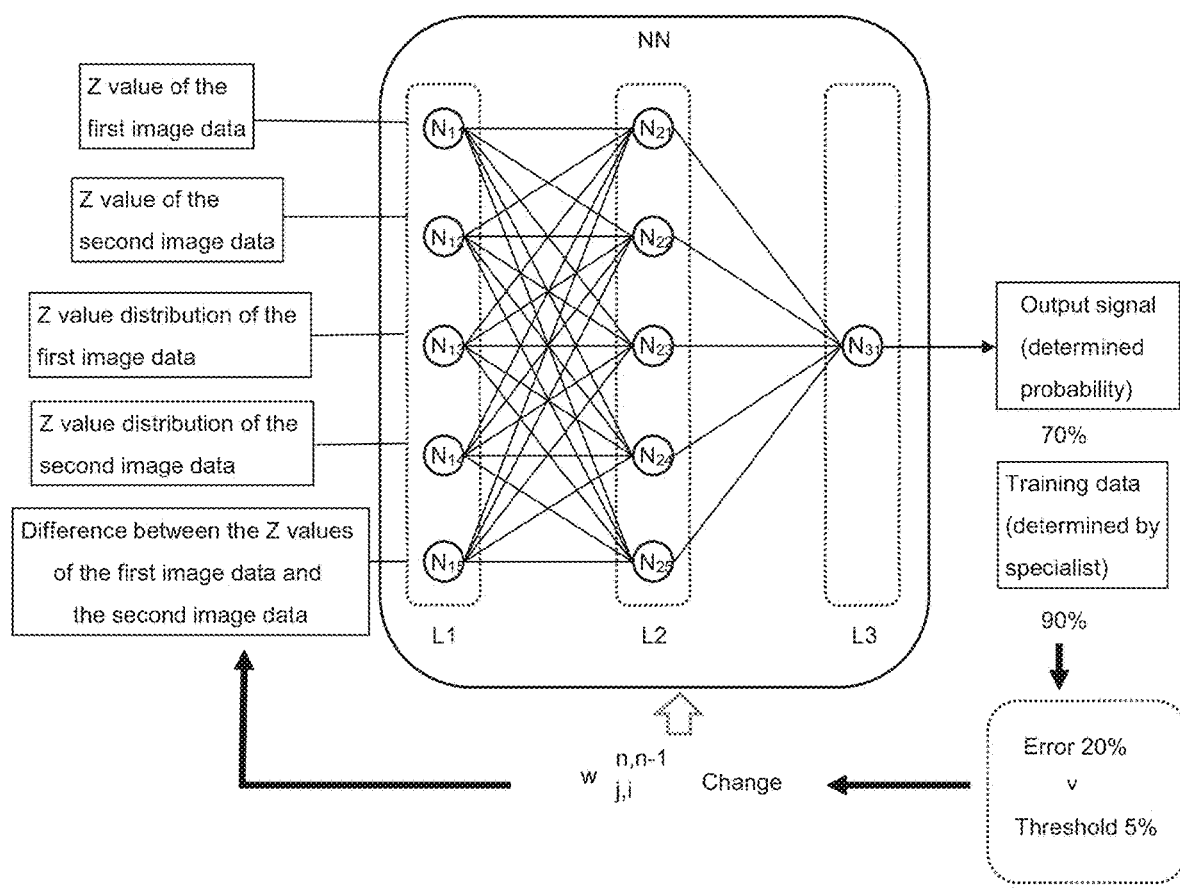
FIG. 7 is a conceptual diagram explaining execution of machine learning in S5 of FIG. 2.

As shown in FIG. 7, the machine learning execution unit 4 sets a weight w which value is, for example, −1 to 1 to each calculation node N constituting a neural network having the same configuration as the neural network shown in FIG. 5. At this time, in order to reduce the influence of the weight w, the absolute value of the weight w is preferably set small initially. Then, five kinds of parameter sets are input into the neural network. In the present embodiment, the parameters input into the neural network include the Z value of the first image data, the Z value of the second image data, the Z value distribution of the first image data, the Z value distribution of the second image data, and the difference between the Z values of the first image data and the second image data. Here, the Z value of the first image data and the second image data is Z value in each pixel. And the distribution of the Z value of the first image data and the second image data is the distribution of the Z value in each image data (300 pixels×300 pixels). Further, the difference between the Z values of the first image data and the second image data is the difference between the Z values of the corresponding pixels of the first image data and the second image data or the sum of the differences in the Z values of corresponding pixel in each image data.

Then, the output signal from the neural network is compared with the training data, and when the difference (hereinafter, referred to as an error) between the output signal and the training data is equal to or more than a predetermined threshold value, the weight w is changed and the five kinds of parameter sets are input into the neural network again. At this time, the weight w is changed by a known error propagation method or the like. By repeating this calculation (i.e. executing machine learning), the error between the output signal from the neural network and the training data given in advance is minimized. At this time, the number of times of machine learning is not particularly limited, and can be, for example, 1000 times to 20000 times. Here, machine learning should be stopped when the error falls below a predetermined threshold or at the operator's arbitrary timing, even if the error between the actual output signal and the pre-given training data is not minimized.

Then, when the machine learning ends, the machine learning execution unit 4 sets the weight of each calculation node N at this time in the neural network. Then, the weight w set by the machine learning execution unit 4 is transmitted to a storage unit (not shown) provided in the system 10 and is used as the weight w of each calculation node N of the neural network in FIG. 5. In this embodiment, the weight w is stored in a storage unit such as a memory provided on the neural network in FIG. 5. Here, by making the configuration of the neural network of FIG. 7 same as that of the neural network of FIG. 5, the weight w set by the machine learning execution unit 4 can be used as it is.

2. SECOND EMBODIMENT

A second embodiment of the present invention will be described with reference to FIG. 8 to FIG. 12. The description of the same configuration and function as those of the first embodiment will not be repeated.

Figure 8:
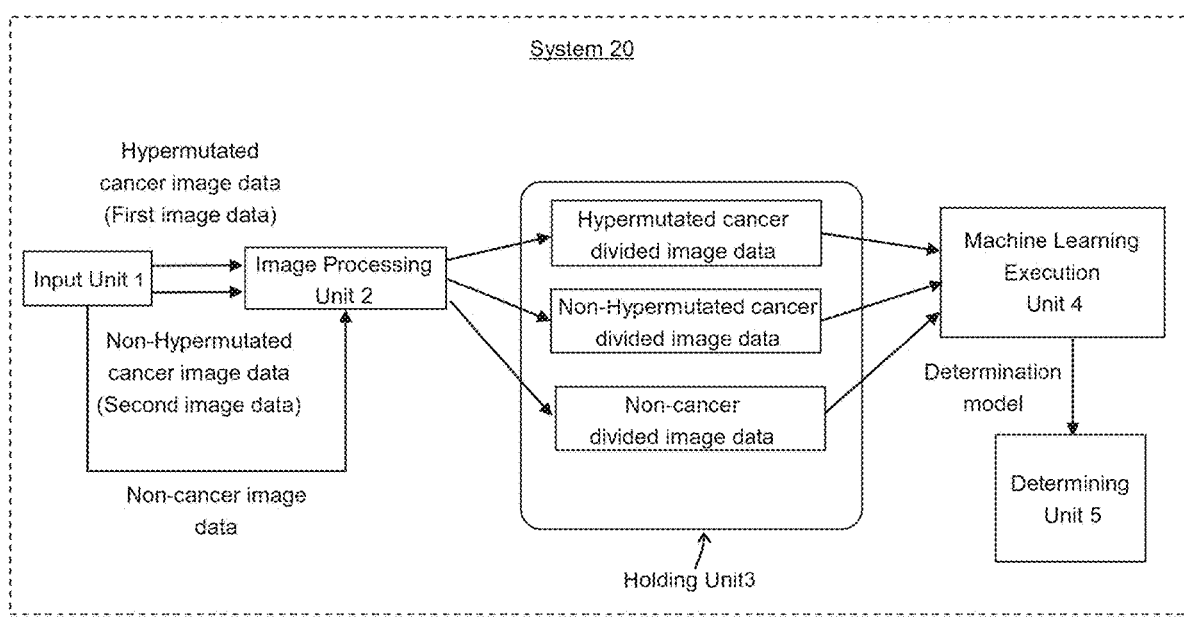
FIG. 8 is a functional block diagram of a system 20 according to the second embodiment.

As shown in FIG. 8, in the system 20 according to the second embodiment, the input unit 21 is configured to be capable of further inputting non-cancer image data in addition to the first image data and the second image data. Here, non-cancer image data means image data other than a pathological section of cancer. The image processing unit 22 performs division process on the input image data. Details of the division process will be described later.

The holding unit 23 is configured to be capable of further holding the divided non-cancer image data in addition to the divided first image data and divided second image data. The machine learning execution unit 24 uses the first image data, the second image data, and the non-cancer image data held by the holding unit 3 as training data to generate determination model (hereinafter, the first determination model) determining whether the image data represents a cancer image or not, and a determination model (hereinafter, the second determination model) determining whether an image of a cancer represents hypermutated cancer or not. The determining unit 25 inputs the third image data into the first and second determination models, and determines whether the third image data represents a cancer image and whether the third image data represents hypermutated cancer.

Figure 9:
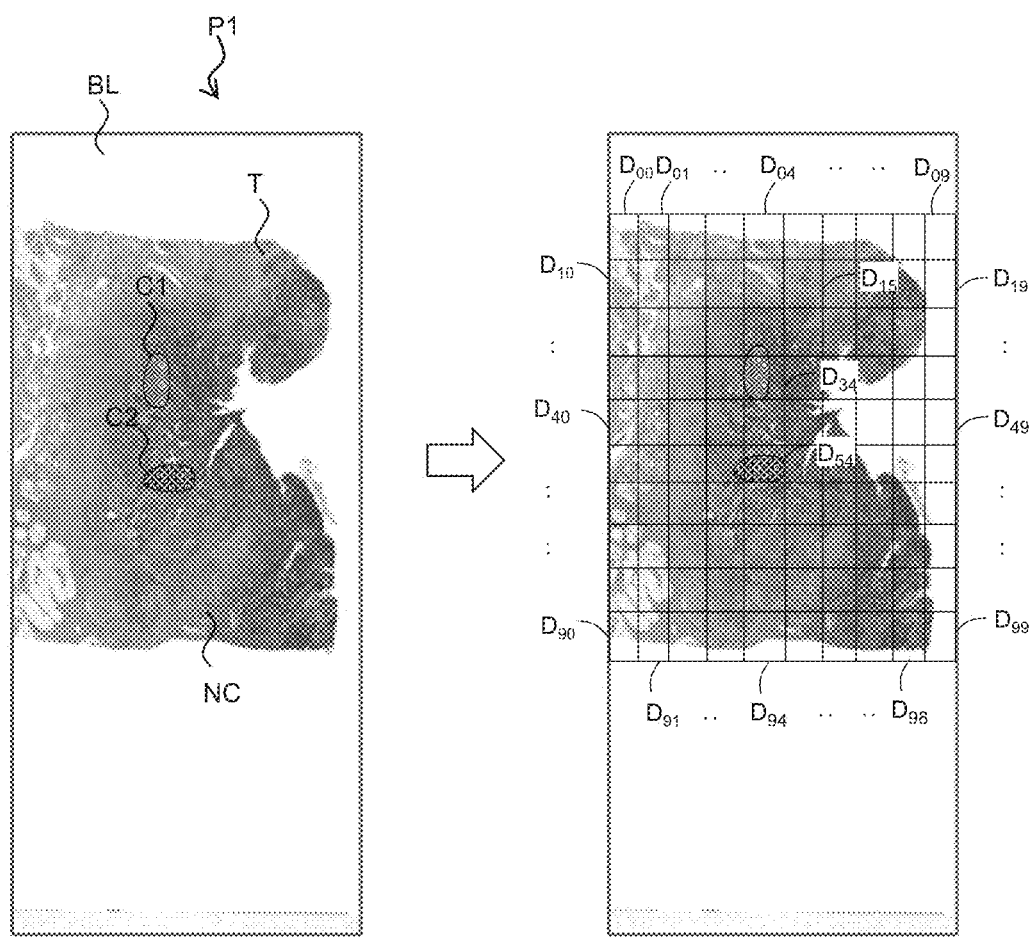
FIG. 9 is a diagram illustrating a division process of an input image in an image processing unit 22.

FIG. 9 shows image data P as an example input to the input unit 21. The image data P has a tissue region T and a blank region BL (for example, a prepared slide region). The tissue region T includes a cancer region C1 that is not hypermutated type cancer, a region C2 that is hypermutated type cancer, and a tissue region NC that is not cancer.

The image processing unit 22 performs division process on the image data P input to the input unit 21. In the example shown in FIG. 9, the tissue region T is divided into 100 pieces of vertically 10 by horizontally 10. That is, 100 tiles D00 to D99 are set to include the tissue region T.

In this example, the tile of the hypermutated type cancer region C2 (for example, tile D54) corresponds to the first image data, and the tile of Non-hypermutated cancer region C1 (for example, the tile D34) corresponds to the second image data. Further, a tile of only non-cancer tissue region NC (for example, tile D15), a tile of only blank region BL (for example, tile D49), and a tile including the non-cancer tissue region NC and the blank region BL (for example, tile D04) correspond to non-cancer image data.

As described above, in the present embodiment, machine learning is performed by inputting various images as the non-cancer image data such as the tile of only non-cancer tissue region NC, the tile of only blank region BL, and the tile including the non-cancer tissue region NC and the blank region BL. By increasing the variety of non-cancer images in this way, the accuracy of determining whether the inspection target data is cancer image or not is improved.

Figure 10:
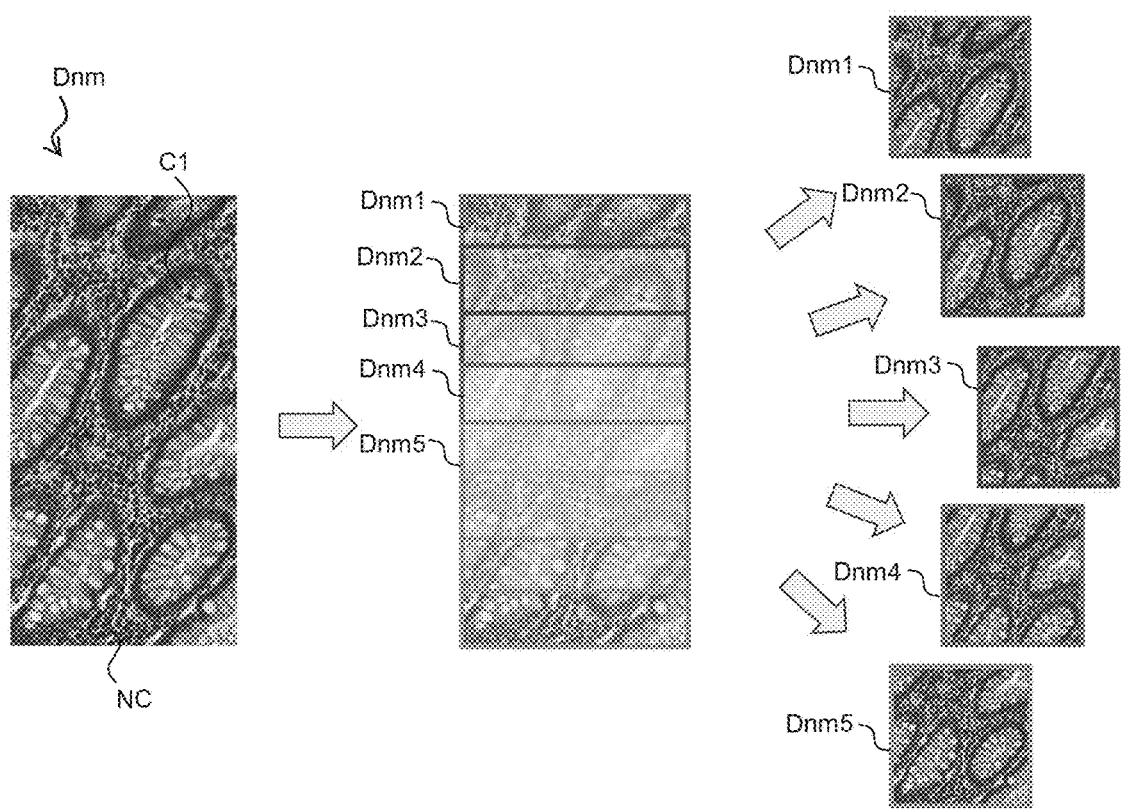
FIG. 10 is also a diagram illustrating a division process of an input image in an image processing unit 22.

Further, in the present embodiment, further division process (hereinafter referred to as second division process) can be performed on the image data after the above described division process (hereinafter referred to as first division process). In FIG. 10, the tile Dnm after being divided by the first dividing process is further divided into five tiles. Here, in the second division process, the division process is performed so that some areas of the tiles after division process overlap with each other. That is, the tile Dnm1 and the tile Dnm2 after the second division process overlap with each other. In addition, the tile Dnm2 and the tile Dnm3 also overlap with each other.

In this way, it is possible to increase the number of images by performing the division process so that some areas overlap in the divided images. As a result, the learning efficiency in the subsequent machine learning can be improved.

Figure 11:
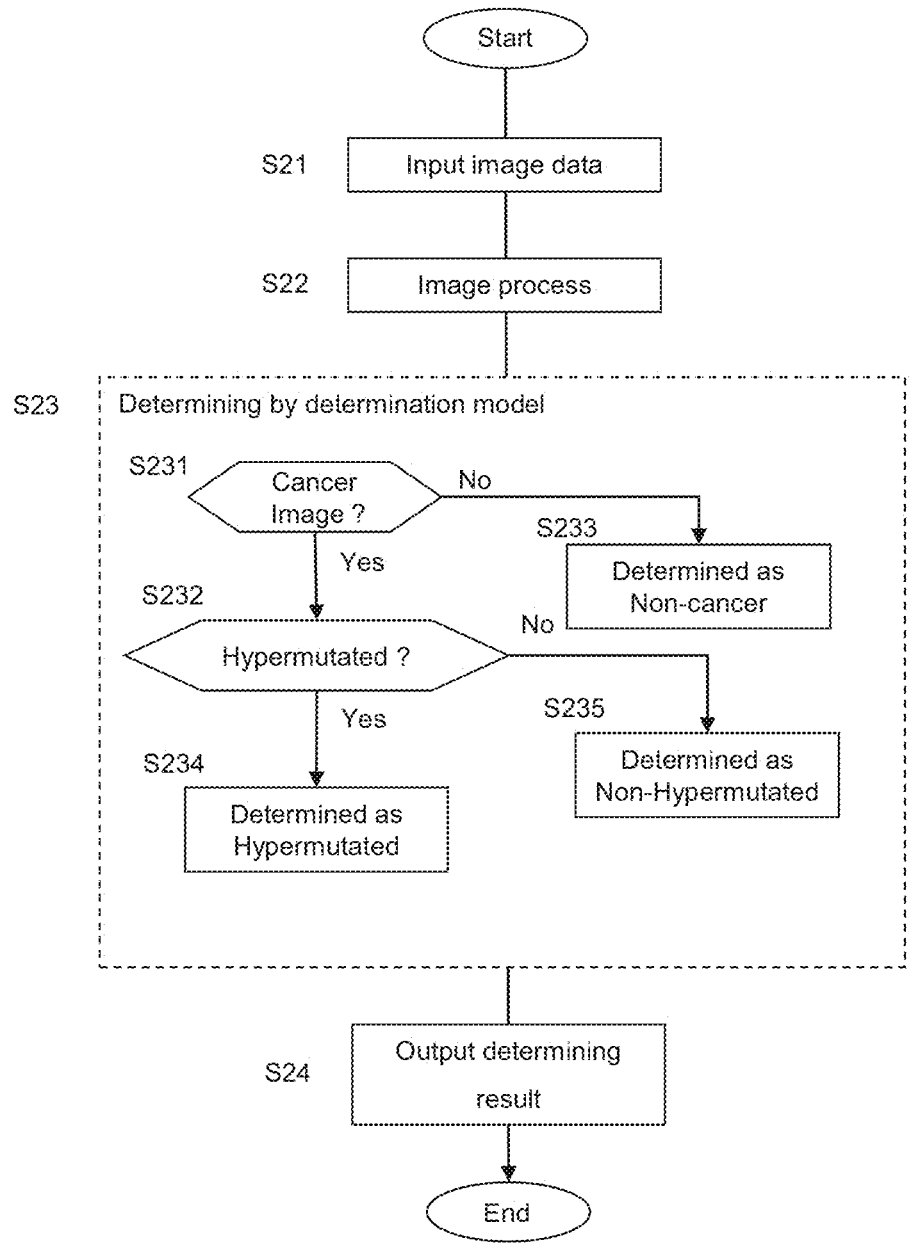
FIG. 11 is a flowchart showing a determining process of third image data according to the present embodiment.

FIG. 11 is a flowchart of the determining process of the third image data in this embodiment. As shown in FIG. 11, in the present embodiment, the determining unit 25 determines whether the third image data represents cancer image or not and whether the third image data represents hypermutated type cancer image or not.

Specifically, at step S231 in step S23, the determining unit 25 determines whether the third image data represents a cancer image or not. If it is not a cancer image (No at step S231), third image data is determined to be a non-cancer image at step S233.

On the other hand, if the image is a cancer image (Yes at step S231), the determining unit 25 determines at step S232 whether the third image data is an image of a hypermutated type cancer or not. If the cancer is not a hypermutated type cancer (No at step S232), the third image data is determined to be an image of the non-hypermutated type cancer at step S234. On the other hand, if the cancer is a hypermutated type cancer (Yes at step S232), the third image data is determined to be an image of the hypermutated type cancer at step S234.

In this way, in this embodiment, it is determined whether the third image data is a cancer image or not and whether the third image data represents a hypermutated cancer or not. Therefore, it is not necessary for the pathologist or the like to previously diagnose whether or not the image data is cancer image data, and the work efficiency in the determining process can be improved.

Here, the determination unit 25 can determines whether the cancer is a hypermutated type cancer or not based on the ratio of the image data which is determined to be hypermutated cancer image in the image data determined to be cancer image.

Figure 12:
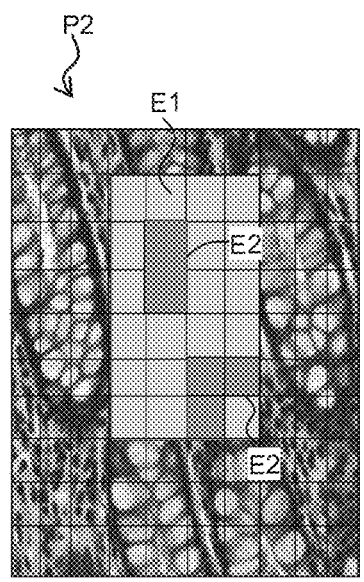
FIG. 12 is a diagram illustrating a determining process in a determining unit 25.

In the example shown in FIG. 12, in the third image data P2, the image E2 determined to be hypermutated type cancer image exists in the image E1 determined to be cancer image. At that time, the determining unit 25 determines that the region indicated by the image E1 has the hypermutated type cancer when the ratio determined by (the number of tiles of E2)/(the number of tiles of E1) is larger than a predetermined threshold value.

By doing this, it becomes possible to remove false positives that are locally identified to be hypermutated type cancer as noise. As a result, it is possible to improve the accuracy of the determination.

As described above, in the second embodiment, the input unit 21 is configured to be capable of further inputting non-cancer image data, and the machine learning execution unit 24 also uses the non-cancer image data as training data to generate determination model determining whether an image data represents a pathological sections of cancer. Then, the determination unit 25 is further configured to be capable of determining whether the third image data is cancer image data or not. With such a configuration, it is not necessary for the pathologist or the like to diagnose whether or not the image data is cancer image data, and the work efficiency in the determining process can be improved.

3. OTHER EMBODIMENTS

Various embodiments have been described above, and the present invention can be implemented in the following modes.

Provided is a program for causing a computer to perform a process comprising, inputting a plurality of first image data and a plurality of second image data, wherein the first image data represents an image of a pathological section of stained hypermutated cancer and the second image data represents an image of a pathological section of cancer which is not hypermutated, and is stained same as the pathological section of the first image data, holding a first image data and a second image data, and generating a determination model determining whether a cancer is hypermutated or not, using the first image data and the second image data held by the holding unit as training data.

Further provided is a method of determining hypermutated cancer performed by the system described above. The hypermutated type cancer referred to herein includes any cancer type, for example, brain tumor, head and neck cancer, breast cancer, lung cancer, esophageal cancer, gastric cancer, duodenal cancer, appendiceal cancer, colon cancer, rectal cancer, liver cancer, pancreatic cancer, gallbladder cancer, bile duct cancer, anal cancer, renal cancer, ureteral cancer, bladder cancer, prostate cancer, penile cancer, testicular cancer, uterine cancer, ovarian cancer, vulvar cancer, vaginal cancer, skin cancer, etc. and it is not limited to these. For the purposes of the present invention, the hypermutated cancer is preferably colon cancer, lung cancer, gastric cancer, melanoma (malignant melanoma), head and neck cancer, or esophageal cancer.

Further provided is a method of determining hypermutated cancer performed by the program described above.

Further provided is a method including the process of determining the effectiveness of immune checkpoint inhibitors described above. Such a method can further include a process of showing that a patient determined to have a hypermutation type cancer has high efficacy of administration of an immune checkpoint inhibitor. Since hypermutated cancers have many cancer-specific antigens that are targets of the immune system, it has been shown that therapies that block the immunosuppressive signal pathway are highly effective. Such a determining method is advantageous because it can be easily discriminated that the cancer is a hypermutated. Here, "the immunity checkpoint" is well known in the art (Naidoo et al. British Journal of Cancer (2014) 111, 2214-2219), such as CTLA4, PD1, and its ligand PDL-1. Also, TIM-3, KIR, LAG-3, VISTA, and BTLA can be listed. Inhibitors of the immune checkpoint block their normal immune function. For example, Inhibitors negatively regulate the expression of a molecule at the immune checkpoint, or bind to that molecule and inhibit it by blocking normal receptor/ligand interactions. Since immune checkpoints act to brake the immune system's response to antigens, the inhibitor diminishes this immunosuppressive effect and enhances the immune response. Inhibitors of immune checkpoints are known in the art, and preferred are anti-CTLA-4 antibodies (such as ipilimumab, tremelimumab), anti-PD-1 antibodies (such as nivolumab), pembrolizumab, pidilizumab, and RG7446 (Roche)), and anti-PDL-1 antibody (such as BMS-936559 (Bristol-Myers Squibb), MPDL3280A (Genentech), MSB0010718C (EMD-Seromo), and MED14736 (AstraZeneca)) and other anti-immune checkpoint antibodies.

Also, the holding unit 3 can be implemented in the form of cloud computing provided in an information processing device such as an external PC or a server. In this case, the external information processing device transmits the necessary data to the system 10 each time the calculation is performed.

Further provided is a non-transitory computer-readable storage medium storing the program described above. Further, provided is an ASIC (application specific integrated circuit), an FPGA (field-programmable gate array), and a DRP (Dynamic Reconfigurable Processor) implementing the functions of the programs described above.

1,21: Input unit
2,22: Image processing unit
3,23: Holding unit
4, 24: Machine learning execution unit
5,25: Determining unit
10, 20: System

The invention claimed is:

1. A system for determining hypermutated cancer comprising:
    an input unit configured to be capable of inputting a plurality of first image data, a plurality of second image data and a plurality of third image data, wherein
    the first image data represents an image of a pathological section of stained hypermutated cancer,
    the second image data represents an image of a pathological section of cancer which is not hypermutated, and is stained same as the pathological section of the first image data, and
    the third image data represents an image of a pathological section of cancer which is newly determined whether hypermutated or not, and is stained same as the pathological section of the first image data;
    a holding unit configured to be capable of holding a first image data and a second image data;
    a machine learning execution unit configured to be capable of generating a determination model determining whether a cancer is hypermutated or not, using the first image data and the second image data held by the holding unit as training data; and
    a determining unit configured to be capable of determining whether the third image data represents an image of hypermutated cancer or not, by inputting the third image data into the determination model.

2. The system of claim 1, wherein
a method of staining the pathological section is hematoxylin eosin staining.

3. The system of claim 1,
the input unit is configured to be capable of further inputting non-cancer image data,
the non-cancer image data represents an image which is not a pathological section of cancer,
the holding unit is configured to be capable of further holding the non-cancer image data,
the machine learning execution unit is configured to be capable of further generating a determination model determining whether an image represents a pathological section of cancer or not, using the non-cancer image data held by the holding unit as training data,
the determining unit is configured to be capable of further determining whether the third image data represents an image of cancer or not.

4. The system of claim 1, further comprising:
an image processing unit configured to be capable of performing a Z value conversion process for at least one of the first image data, the second image data and the non-cancer image data, converting each RGB color in each pixel into Z value in the CIE color system based on the entire color distribution of the first image data, the second image data or the non-cancer image data.

5. The system of claim 4, wherein
the image processing unit is configured to be capable of performing a division process dividing at least one of the first image data, the second image data, and the non-cancer image data input into the input unit.

6. The system of claim 5, wherein
the image processing unit performs the division process such that a part of the regions in a divided image overlaps each other.

7. The system of claim 5,
the image processing unit is configured to be further capable of performing a division process dividing the third image data input into the input unit.

8. The system of claim 3, wherein
the determining unit determines whether the third image data represents an image of a pathological section of cancer or not, and further determines whether the image data determined as a cancer image data represents an image of hypermutated cancer or not.

9. The system of claim 8, wherein
the determining unit determines whether a cancer image data represents an image of hypermutated cancer or not, based on the ratio of the image data determined as an image of hypermutated cancer in the cancer image data.

10. A non-transitory computer-readable storage medium storing a program for causing a computer to perform a process comprising:
inputting a plurality of first image data and a plurality of second image data, wherein
the first image data represents an image of a pathological section of stained hypermutated cancer and
the second image data represents an image of a pathological section of cancer which is not hypermutated, and is stained same as the pathological section of the first image data;

holding a first image data and a second image data; and generating a determination model determining whether a cancer is hypermutated or not, using the first image data and the second image data held by the holding unit as training data.

11. The method of determining hypermutated cancer performed by the system of claim 1.

12. The method of determining hypermutated cancer performed by the program stored in the storage medium of claim 10.

13. The method of claim 11 including the process of determining the effectiveness of immune checkpoint inhibitors.

* * * * *